(12) United States Patent
Higgins et al.

(10) Patent No.: US 11,406,370 B2
(45) Date of Patent: Aug. 9, 2022

(54) HANDLE FOR RETRACTOR BLADE

(71) Applicant: BOSS INSTRUMENTS, LTD., INC., Gordonsville, VA (US)

(72) Inventors: Sean Higgins, Midlothian, VA (US); John Ryall, Gordonsville, VA (US); Peter Fetzer, Oehningen-Wangen (DE)

(73) Assignee: BOSS INSTRUMENTS, LTD., INC., Gordonsville, VA (US)

( * ) Notice: Subject to any disclaimer, the term of this patent is extended or adjusted under 35 U.S.C. 154(b) by 0 days.

(21) Appl. No.: 17/441,061

(22) PCT Filed: Mar. 9, 2020

(86) PCT No.: PCT/US2020/021647
§ 371 (c)(1),
(2) Date: Sep. 20, 2021

(87) PCT Pub. No.: WO2020/190551
PCT Pub. Date: Sep. 24, 2020

(65) Prior Publication Data
US 2022/0142631 A1    May 12, 2022

Related U.S. Application Data

(60) Provisional application No. 62/820,666, filed on Mar. 19, 2019.

(51) Int. Cl.
*A61B 17/02* (2006.01)
*A61B 17/00* (2006.01)

(52) U.S. Cl.
CPC ...... *A61B 17/02* (2013.01); *A61B 2017/0046* (2013.01)

(58) Field of Classification Search
CPC .. A61B 17/02; A61B 17/0206; A61B 17/0218
(Continued)

(56) References Cited

U.S. PATENT DOCUMENTS

| 6,196,969 | B1 | 3/2001 | Bester et al. |
| 8,216,241 | B2 * | 7/2012 | Runco ................ A61B 17/7032 606/104 |

(Continued)

FOREIGN PATENT DOCUMENTS

EP    0 101781    3/1984

OTHER PUBLICATIONS

International Search Report for PCT/US2020/021647 dated May 11, 2020, 3 pages.

(Continued)

*Primary Examiner* — Si Ming Ku
(74) *Attorney, Agent, or Firm* — Joshua B. Brady; Nixon & Vanderhye, P.C.

(57) ABSTRACT

A retractor system includes one or more blades, a handle, and a frame. The handle includes first and second arms with jaw portions and recesses configured to removably retain a blade. Both arms include rotatable connections and handles, where the rotatable connections are between jaw portions and handles. The rotatable connections are connected together such that the arms are rotatable with respect to one another. In one embodiment, the recesses are partial disc shapes opposed to one another, such that when the jaw portions are in a closed position, a disc-shaped space is present between the jaw portions in the closed position. The blade includes a corresponding disc-shape protrusion that may be retained in the recesses, and in some embodiments may include one or more notches to mate with a protrusion in a recess that prevents blade rotation while in the handle.

37 Claims, 13 Drawing Sheets

(58) Field of Classification Search
USPC .......................................................... 600/210
See application file for complete search history.

(56) References Cited

U.S. PATENT DOCUMENTS

2010/0256454 A1* 10/2010 Farley .................... A61B 17/02
600/210
2012/0271118 A1   10/2012 White

OTHER PUBLICATIONS

Written Opinion of the ISA for PCT/US2020/021647 dated May 11, 2020, 7 pages.

* cited by examiner

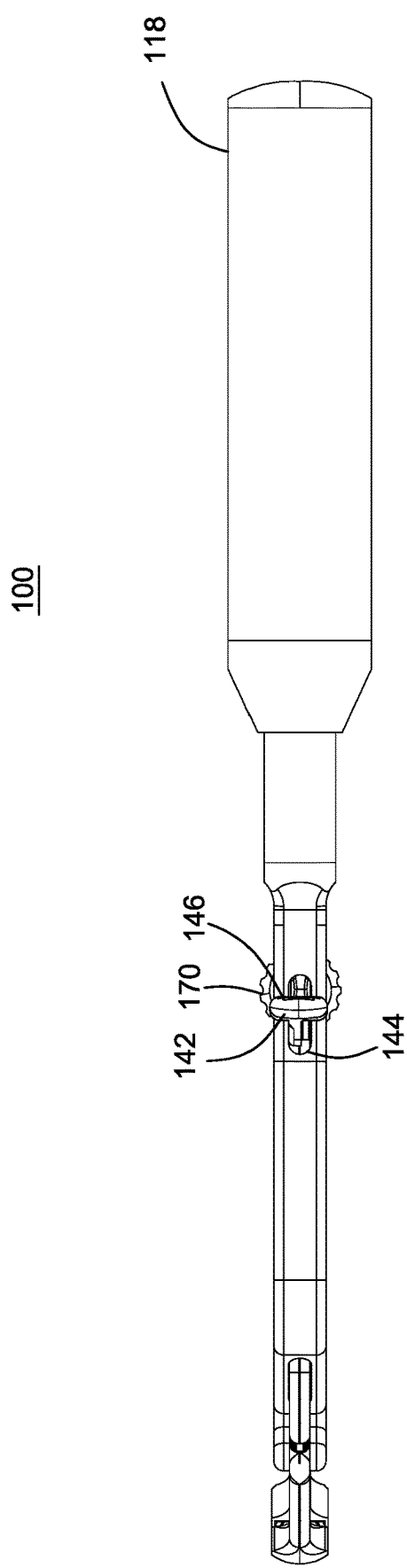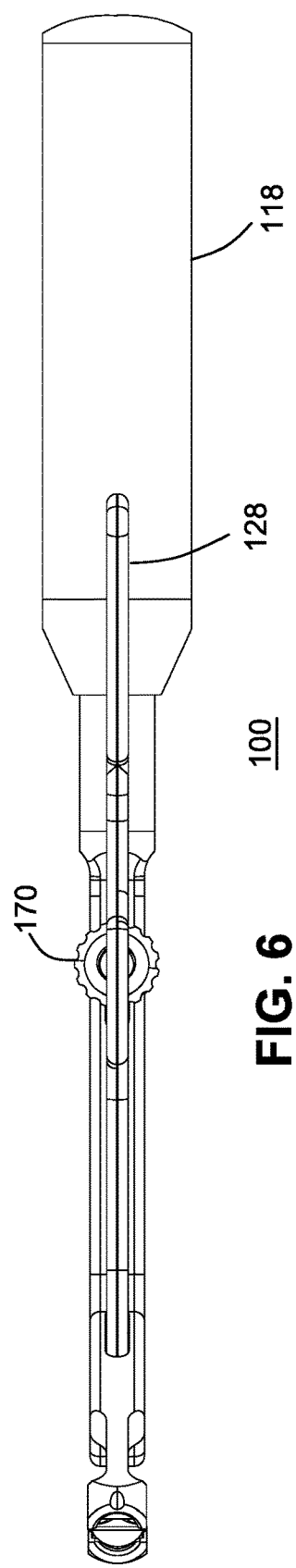
FIG. 5
FIG. 6

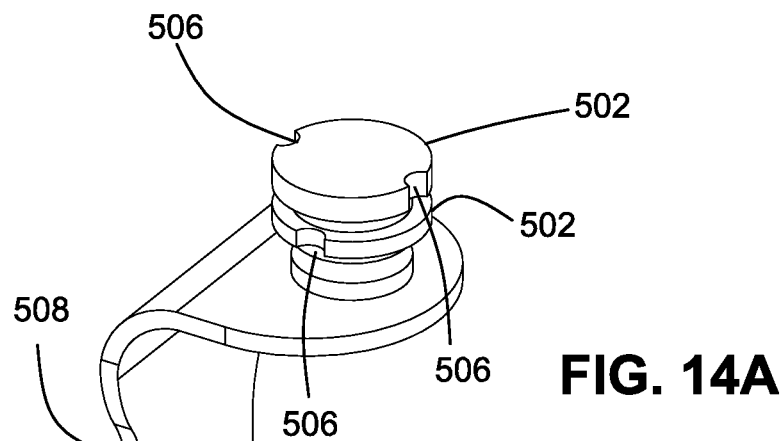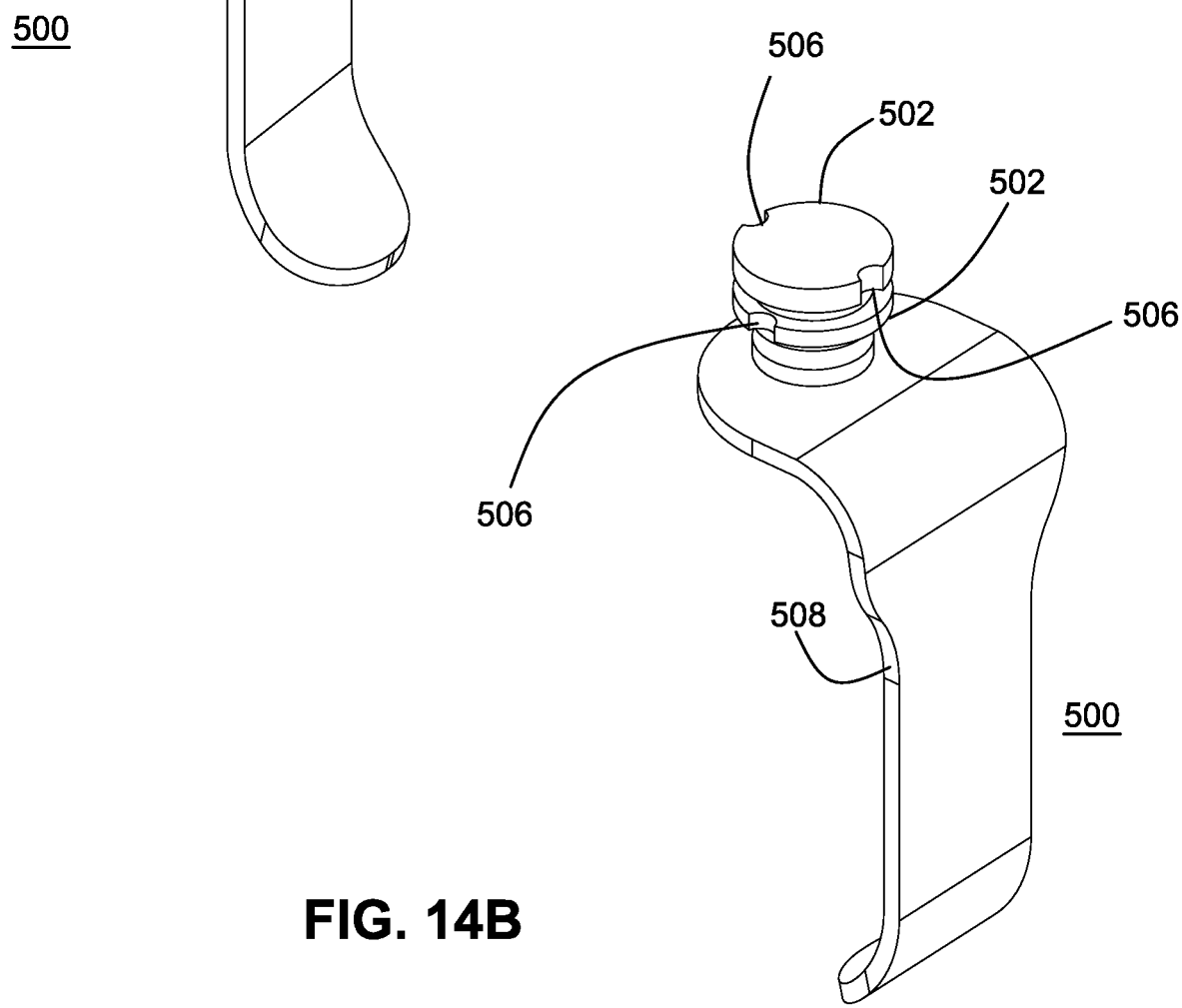

HANDLE FOR RETRACTOR BLADE

This application is the U.S. national phase of International Application No. PCT/US2020/021647 filed Mar. 9, 2020 which designated the U.S. and claims priority to U.S. Provisional Patent Application No. 62/820,666 filed Mar. 19, 2019, the entire contents of each of which are hereby incorporated by reference.

BACKGROUND

In surgery that requires access to internal organs and other anatomical structures, retractors are often used to hold tissue open at an incision, to expose the area for the surgery and provide adequate space for surgical instruments and the procedure. A retractor typically includes one or more retractor blades, each blade having a retractor shaft or hub upon which the retractor blade is mounted. The retractor is removably connected to a retractor support or frame, often by a clamping device. One type of retractor system includes one or more blades for contacting tissue, a handle, and a frame. Each blade is separable from the handle and the frame. With this type of retractor system, the handle may be used to position a blade in the desired position (e.g., relative to the incision and tissue), the frame can be configured as needed around the incision and the operating table, and then the blade can be transferred from the handle to the frame. This type of retractor system allows for convenient retractor blade positioning during initial setup procedures, as well as securing the retractor blade in the desired or predetermined position for the remainder of the procedure.

One drawback in contemporary retractor systems is the freedom of the retractor blade to rotate in the handle, during transfer from handle to frame, and even in the frame. Surgical procedures demand that retractor shafts have a low profile, such that the shaft has minimal extension above the retractor frame when connected to the frame. This provides more clearance and space for the surgical procedure, and limits structures that might interfere with the procedure. As a consequence, there is limited shaft surface area available for the handle to engage the retractor shaft and for the retractor frame to engage the shaft—particularly during retractor shaft transfer from handle to frame (and vice versa). Contemporary retractor systems have struggled to accommodate the handle and frame connections to the retractor shaft, particularly with respect to preventing the retractor shaft and blade from rotating. The potential for a blade to rotate during positioning with the handle, transferring from handle to retractor frame, and even after connected to the retractor frame, can interfere with surgical procedures. What is needed, then, are improved retractor systems in which the retractor shaft or hub fixedly engages both the handle and the frame, without rotating when engaged.

BRIEF SUMMARY

The present approach allows for retractor systems having a retractor blade with a shaft or hub, a retractor handle, and a retractor frame. With prior art retractor systems, the blade may rotate relative to the handle, and/or relative to the frame. Such rotation is desirable for some users or uses. However, rotation of the blade relative to the handle may be undesirable for other users or uses. The present approach advantageously overcomes this and other issues present in prior art systems.

The present approach relates to a handle that can removable engage a retractor blade. The handle may be used, for example, to position the blade in the desired location, and hold the blade in that location until the retractor frame is setup and ready to receive the retractor blade. The handle may connect to the retractor blade so that the retractor blade may rotate relative to the handle, or the handle may connect to the retractor blade to prevent relative rotation of the blade with respect to the handle, or the handle may connect to the retractor blade to both allow and prevent rotation, depending upon a changeable configuration of the handle and the user's preference.

The handle may include movable opposed jaws that are configured to retain a predetermined portion of the retractor blade, such as an upper portion of a retractor shaft or hub. The handle jaws may be pivotably fixed to one another. The handle may be lockable, such that the jaws are positionally fixed with respect to one another when the handle is locked. In the locked position, the handle retains the blade without requiring the user to apply force on the handle, advantageously allowing the user to manipulate the blade's position, and maintain that position, with minimal effort. The locked position may be adjustable in some embodiments, which may allow the jaws to prevent or allow rotation of the blade with respect to the handle, depending on the user's preference.

The jaws may have a shape that is configured to grasp a predetermined portion of the blade, such as an upper portion of the blade shaft or hub. The shape may be a recess in one or both jaws that is a negative of the predetermined portion of the blade. The predetermined portion of the blade may be, for example, a disc shape and the recess may be a disc-shaped recess. Of course, other corresponding shapes may be used without deviating from the present approach. With such shapes, the jaws may engage the predetermined portion of the blade with a first force to allow rotation of the blade, or if desired the handle jaws may engage the predetermined portion with a second force, greater than the first force, to generate sufficient frictional forces to prevent rotation.

In some embodiments, the blade and one or both of the jaws may include a male/female mating relationship that, when engaged, prevents rotation of the blade with respect to the handle. This feature may be in addition to disc-shaped member discussed above. For example, the blade may include a plurality of protrusions and spaces between adjacent protrusions, and one or both of the jaws may include a protrusion adapted to fit into the spaces. Some embodiments of the blade may include a member on the shaft or hub that is substantially gear-shaped, and the jaws may include a corresponding protrusion, or multiple protrusions, that fit into the spaces between the gear teeth. For example, the protrusion may be a cylinder or the protrusion may be a pin, which may be cylindrical, inserted into a hole in one of the jaws. The gear-shaped member and the disc-shaped member may share a common axis. The handle jaws may, when engaged, partially or substantially surround the disc-shaped member, and the protrusion may extend inward from the jaw to engage the gear on the blade shaft or hub. When the jaws are in the closed or engaged position, the protrusion and the axis of the disc and gear-shaped member may be parallel, such that the jaw's protrusion fits into a space between gear teeth on the blade shaft and limits rotational movement of the blade. It should be appreciated that the number and position of the gears and protrusion may allow the handle to engage and hold the blade in more than one orientation.

In a first example, a handle for holding a retractor blade includes a first arm that is rigid. The first arm includes a first jaw portion with a first recess, a first rotatable connection and a first handle portion, the first rotatable connection being between the first jaw portion and the first handle portion. The handle includes a second arm that is rigid. The second arm includes a second jaw portion with a second recess, a second rotatable connection and a second handle portion, the second rotatable connection being between the second jaw portion and the second handle portion. In some embodiments, the first arm and the second arm may include a bend, such that the distal portion of each arm after the bend extends along an axis offset from the axis of proximal portion of the arm before the bend. The bend may be between the rotatable connection and the handle portions, such that the rotatable connection is distal of the bend. The first rotatable connection and the second rotatable connection are connected together such that the first arm and the second arm are rotatable with respect to one another within a predetermined angular range. In some embodiments, the predetermined angular range is such that a user may operate the entire range with one hand. For example, the range may be about 5 degrees to about 45 degrees in some embodiments, and 15 degrees to about 45 degrees in some embodiments, and in other embodiments about 10-15 degrees, about 20-25 degrees, about 30-35 degrees, and about 40-45 degrees. The handle includes a lock mechanism configured to fix a rotational orientation of the first arm to the second arm, such as when the handle is in a closed position. The lock mechanism advantageously allows a user to maintain the closed position without applying force on the handle, which is useful when positioning the blade and holding the blade while the retractor frame is setup. In some embodiments, the lock mechanism may be thumb-activated (e.g., to engage or disengage the lock), to advantageously enable a user to operate the handle with a single hand. The rotational orientation may be adjustable and the closed position may be a subset of the predetermined angular range. The first recess and the second recess are configured to simultaneously receive and retain a disc-shaped member attached to the retractor blade on opposite sides of a diameter of the disc-shaped member. It should be appreciated that modifications may be made without deviating from the present approach. For example, in some embodiments the handle includes a single recess configured to engage a corresponding member on the retractor blade. As another example, the positions of the recess and disc-shape element may be reversed in some embodiments. And in yet another example, the element may have a shape other than a disc, such as one or more protrusions that may be received in corresponding recesses.

In the first example, (a) the first recess and the second recess may be negatives of respective portions of the disc-shaped member; (b) the first jaw portion and the second jaw portion may be together configured to prevent the retractor blade from rotating around a central axis of the disc-shaped member; (c) the first jaw portion and the second jaw portion may be together configured to clamp the disc-shaped member and apply a frictional force that prevents the disc-shaped member from rotating; (d) one of the first jaw portion and the second jaw portion may include a pin adapted to engage a recess of the retractor blade that is adjacent the disc-shaped member to prevent the retractor blade from rotating around a central axis of the disc-shaped member; (e) an axis of the pin may be substantially parallel to the central axis of the disc-shaped member when the disc-shaped member is retained between the first recess and the second recess; (f) the first jaw portion and the second jaw portion are parallel in a closed configuration; (g) the first recess and the second recess may be oriented such that a central axis of the disc-shaped member is parallel to the first jaw portion and the second jaw portion in the closed configuration; (h) the closed position may allow the retractor blade to rotate around a central axis of the disc-shaped member while retaining the disc-shaped member between the first jaw portion and the second jaw portion; (i) the closed position may prevent the retractor blade from rotating around a central axis of the disc-shaped member and retain the disc-shaped member between the first jaw portion and the second jaw portion; (j) the closed position may be selectable from a plurality of closed positions; (k) the lock mechanism may include mated male and female threaded components that provide the plurality of closed positions by relative rotation between the male and female threaded components; (l) the first arm may include a first bend between the first rotatable connection and the first handle portion, and the second arm may include a second bend between the second rotatable connection and the second handle portion; (m) the first bend and the second bend may be a same direction and angle; (n) the lock mechanism may include a first bar with a first rotational connection to the first arm and a second bar with a second rotational connection to the second arm; (o) rotation of the first bar in a direction may allow engagement of the second bar and rotation of the first bar in the direction may cause release of the second bar; (p) the second bar may extend from and transverse to the second arm; (q) the lock mechanism may include an adjustment mechanism to adjust an amount that the second bar extends from the second arm; (r) the adjustment mechanism may include a rotatable knob that is threaded to a third bar such that rotation of the knob causes relative extension or retraction of the third bar, and the third bar provides the second rotational connection; (s) n the second bar may include a yoke that includes the second rotational connection and a portion of the second arm may be retained between the yoke and the third bar; (t) the first arm may include an aperture that contains a portion of the first bar and that is adapted to receive a portion of the second bar when the handle is in the closed position; and/or (u) the portion of the second bar may be retained between a wall of the aperture and the portion of the first bar when the lock mechanism is in a locking position. It should be appreciated that the aperture may be configured to limit the angular range of the first and second arms when in an opened position, thereby advantageously allowing a user to operate the full range with one hand.

In a second example, a handle for holding a retractor blade includes a first arm that is rigid. The first arm includes a first jaw portion with a first recess, a first rotatable connection and a first handle portion, the first rotatable connection being between the first jaw portion and the first handle portion. The handle includes a second arm that is rigid. The second arm includes a second jaw portion with a second recess, a second rotatable connection and a second handle portion, the second rotatable connection being between the second jaw portion and the second handle portion. The first rotatable connection and the second rotatable connection are connected together such that the first arm and the second arm are rotatable with respect to one another. The first recess and the second recess are configured to simultaneously receive and retain a disc-shaped member attached to the retractor blade on opposite sides of a diameter of the disc-shaped member. The disc-shaped member may be a protrusion at an upper portion of a blade shaft or hub. In some embodiments, the protrusion may have a shape other than a disc.

In the second example, (a) the first recess and the second recess may be negatives of respective portions of the disc-shaped member; (b) the first jaw portion and the second jaw portion may be together configured to prevent the retractor blade from rotating around a central axis of the disc-shaped member; (c) the first jaw portion and the second jaw portion may be together configured to clamp the disc-shaped member and apply a frictional force that prevents the disc-shaped member from rotating; (d) one of the first jaw portion and the second jaw portion may comprises a pin adapted to engage a recess of the retractor blade that is adjacent the disc-shaped member to prevent the retractor blade from rotating around a central axis of the disc-shaped member; (e) an axis of the pin may be substantially parallel to the central axis of the disc-shaped member when the disc-shaped member is retained between the first recess and the second recess; (d) the first jaw portion and the second jaw portion may be parallel in a closed configuration; the first recess and the second recess may be oriented such that a central axis of the disc-shaped member is parallel to the first jaw portion and the second jaw portion in the closed configuration; (e) the handle may further include a lock mechanism configured to fix a rotational orientation of the first arm to the second arm when the handle is in a closed position; (f) the closed position may allow the retractor blade to rotate around a central axis of the disc-shaped member while retaining the disc-shaped member between the first jaw portion and the second jaw portion; (g) the closed position may prevent the retractor blade from rotating around a central axis of the disc-shaped member and retain the disc-shaped member between the first jaw portion and the second jaw portion; (h) the closed position may be selectable from a plurality of closed positions; (i) the lock mechanism may include mated male and female threaded components that provide the plurality of closed positions by relative rotation between the male and female threaded components; and/or (j) the first arm may include a first bend between the first rotatable connection and the first handle portion, and the second arm may include a second bend between the second rotatable connection and the second handle portion.

In a third example, a hinged tool includes a first arm with a first rotatable connection and a second arm with a second rotatable connection. The first rotatable connection and the second rotatable connection are connected together such that the first arm and the second arm are rotatable with respect to one another within a predetermined angular range. The hinged tool includes a lock mechanism configured to fix a rotational orientation of the first arm to the second arm only when the hinged tool is in a closed position. The rotational orientation is adjustable and the closed position is a subset of the predetermined angular range. It should be appreciated that the lock mechanism may be incorporated into other embodiments.

In the third example, (a) the lock mechanism may include a first bar with a first rotational connection to the first arm and a second bar with a second rotational connection to the second arm; (b) rotation of the first bar in a direction may allow retention of the second bar and rotation of the first bar in the direction may cause release of the second bar; (c) the second bar may extend from and transverse to the second arm; (d) the lock mechanism may include an adjustment mechanism to adjust an amount that the second bar extends from the second arm; (e) the adjustment mechanism may include a rotatable knob that is threaded to a third bar such that rotation of the knob causes relative extension or retraction of the third bar, and the third bar may provide the second rotational connection; (f) the second bar may include a yoke that includes the second rotational connection and a portion of the second arm may be retained between the yoke and the third bar; (g) the first arm may include an aperture that contains a portion of the first bar and that is adapted to receive a portion of the second bar when the hinged tool is in the closed position; and/or (h) the portion of the second bar may be retained between a wall of the aperture and the portion of the first bar when the lock mechanism is in a locking position.

In a fourth example, a tool includes a first arm that is rigid. The first arm includes a first jaw portion with a first recess, a first rotatable connection and a first handle portion, the first rotatable connection being between the first jaw portion and the first handle portion. The tool includes a second arm that is rigid. The second arm includes a second jaw portion with a second recess, a second rotatable connection and a second handle portion, the second rotatable connection being between the second jaw portion and the second handle portion. The first rotatable connection and the second rotatable connection are connected together such that the first arm and the second arm are rotatable with respect to one another. The first recess and the second recess are each partial disc shapes and opposed to one another when the first jaw and the second jaw are in a closed position such that a disc-shaped space is present between the first jaw and the second jaw in the closed position and a radius of the disc-shaped space is substantially tangential to a path of movement of the first jaw or the second jaw.

In the fourth example, (a) one of the first jaw portion and the second jaw portion may include a protrusion extending perpendicular to the radius of the disc-shaped space, where the protrusion may be a pin inserted into the one of the first jaw portion and the second jaw portion; (b) the first jaw portion and the second jaw portion may be parallel in the closed position; (c) the closed position may be selectable from a plurality of closed positions; (d) the tool may include a lock mechanism configured to fix a rotational orientation of the first arm to the second arm when the tool is in the closed position; (e) the lock mechanism may include a first bar with a first rotational connection to the first arm and a second bar with a second rotational connection to the second arm; (f) rotation of the first bar in a first direction may cause retention of the second bar and rotation of the first bar in a second direction may cause release of the second bar; (g) the second bar may extend from and transverse to the second arm; (h) the lock mechanism may include mated male and female threaded components that provide the plurality of closed positions by relative rotation between the male and female threaded components; (i) the lock mechanism may include an adjustment mechanism to adjust an amount that the second bar extends from the second arm; (j) the adjustment mechanism may include a rotatable knob that is threaded to a third bar such that rotation of the knob causes relative extension or retraction of the third bar, and the third bar provides the second rotational connection; (k) the second bar may include a yoke that includes the second rotational connection such that a portion of the second arm is retained between the yoke and the third bar; (l) the first arm may include an aperture that contains a portion of the first bar and that is adapted to receive a portion of the second bar when the handle is in the closed position; (m) the portion of the second bar may be retained between a wall of the aperture and the portion of the first bar when the lock mechanism is in a locking position; (n) the first arm may include an aperture with the second arm extending through the aperture; (o) the aperture may limit a maximum opening angle of the tool, e.g., through contact between the second arm and a wall or edge of the aperture; (p) the first arm may include a first bend between the first rotatable connection and the first handle portion, (q) the aperture may be between the first rotatable connection and the first bend; (r) the second arm may include a second bend between the second rotatable connection and the second handle portion; (s) the first bend and the second bend may be a same direction and angle; and/or (t) the second bend may be between the aperture and the second rotatable connection when the tool is in the closed position.

It should be appreciated that features described with respect to one embodiment may be included on another embodiment without deviating from the present approach. Other aspects, features, and advantages of this technology will become apparent from the following detailed description when taken in conjunction with the accompanying drawings, which are a part of this disclosure and which illustrate, by way of example, principles of this technology.

BRIEF DESCRIPTION OF THE DRAWINGS

FIG. 5 is a top view of the tool.

FIG. 6 is a bottom view of the tool.

FIGS. 14A and 14B are opposite perspective views of one embodiment of a retractor blade.

DETAILED DESCRIPTION

The following paragraphs describe specific embodiments of the present approach, and is not intended to limit the scope of the present approach. It should be appreciated that modifications may be made to the specific embodiments described herein without deviating from the present approach.

Figure 1:
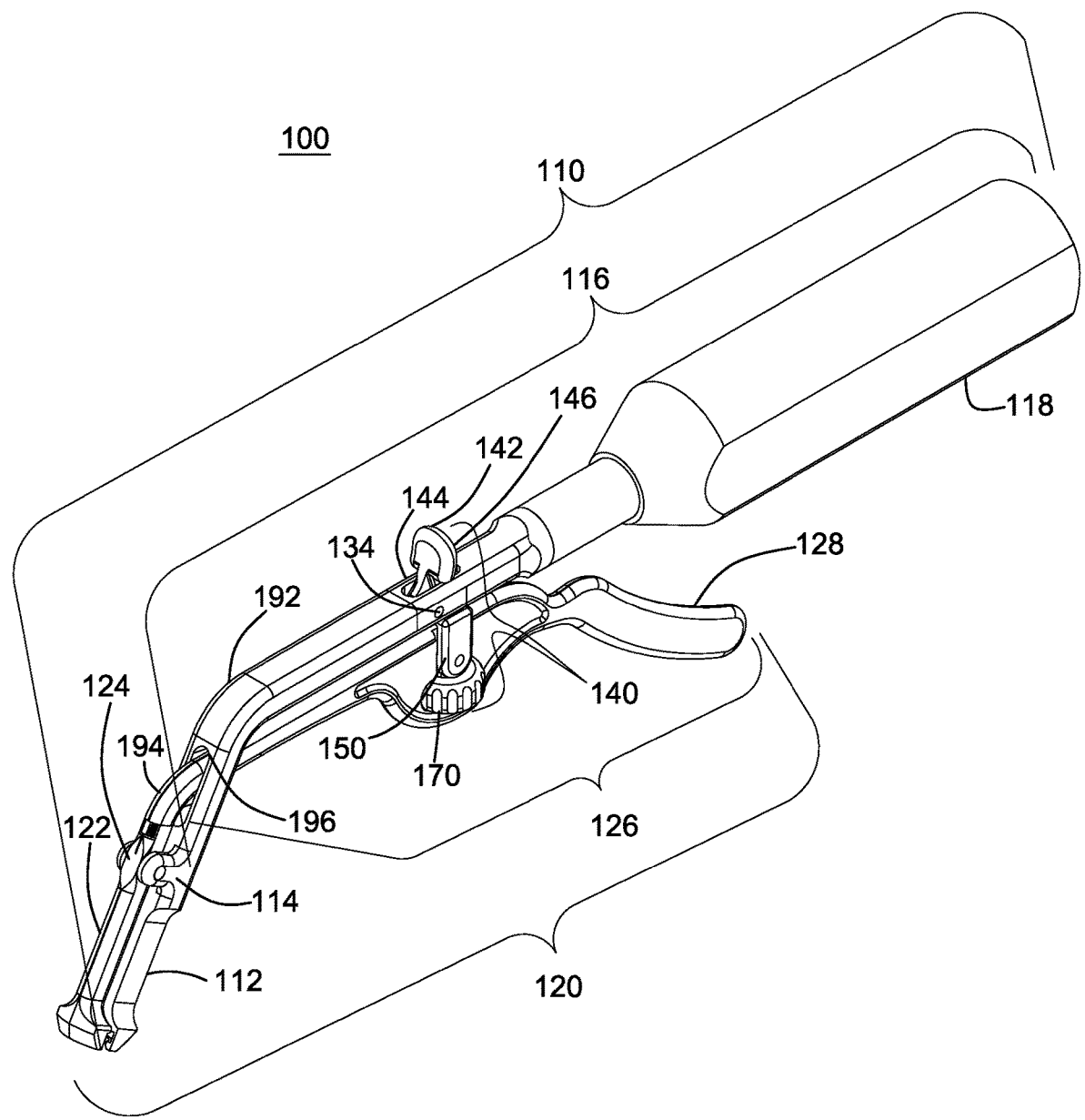
FIG. 1 is a perspective view of an example of a tool according to one embodiment of the present approach.
Figure 2:
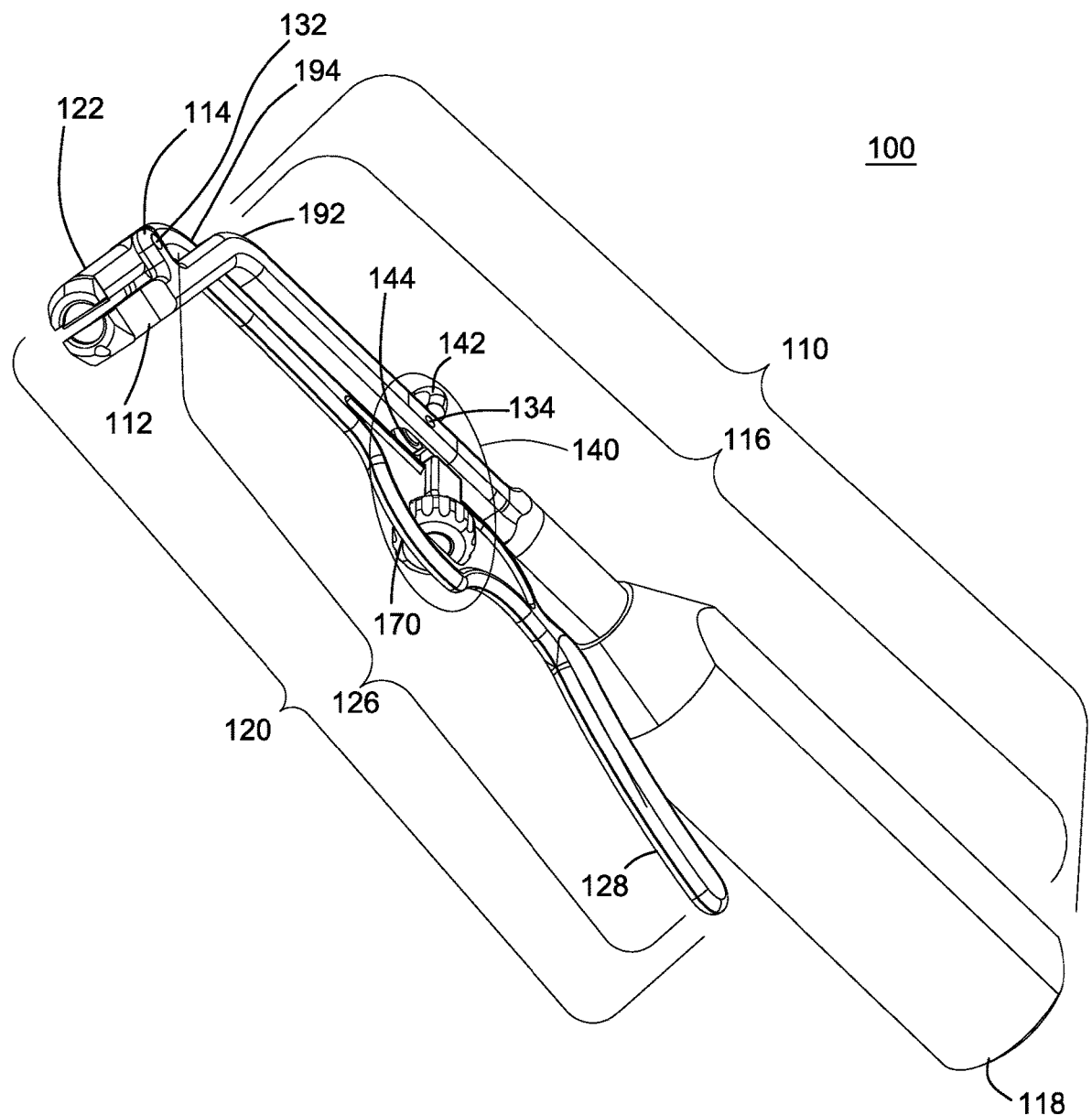
FIG. 2 is a second perspective view of the tool.
Figure 3:
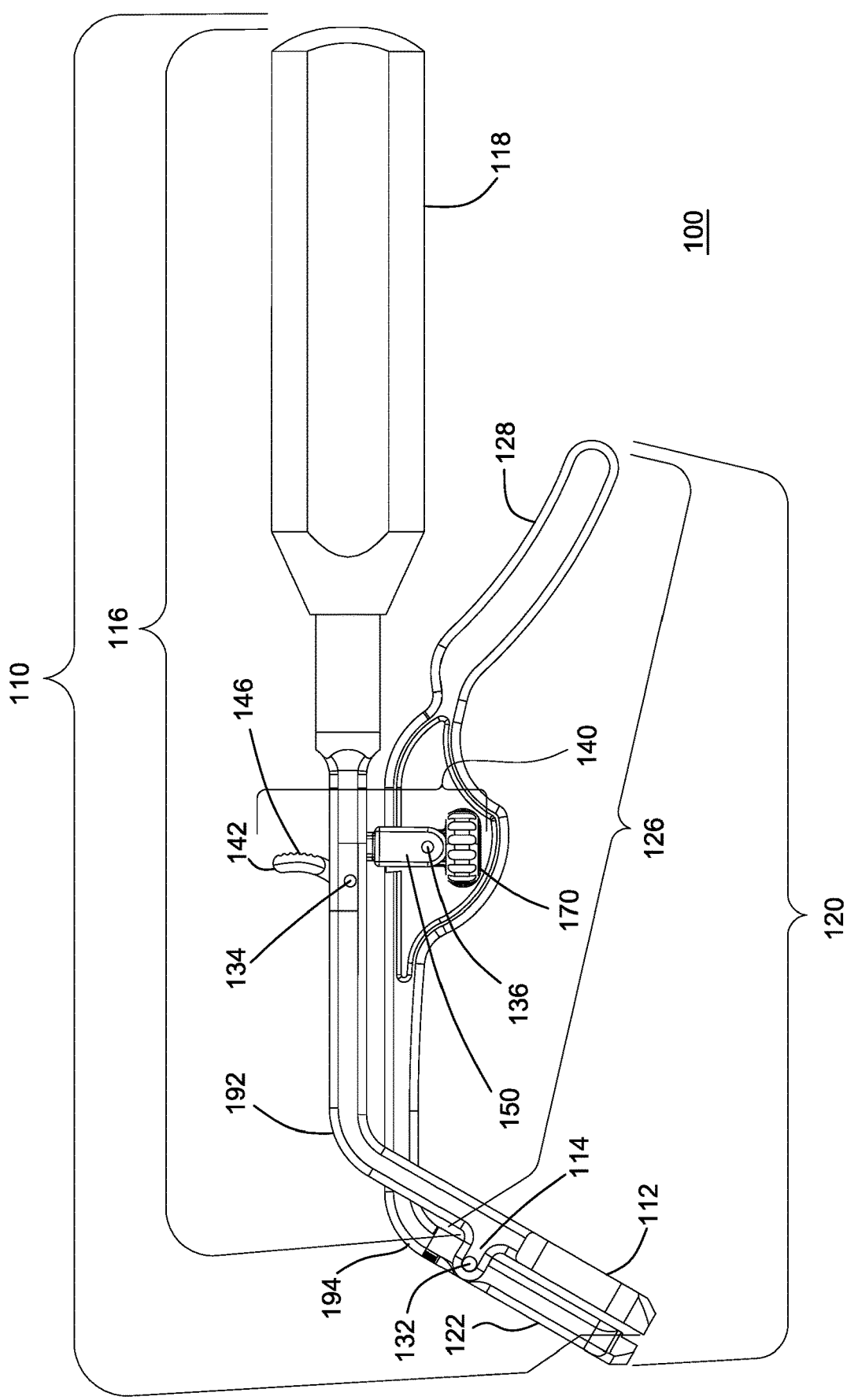
FIG. 3 is a first side view of the tool.
Figure 4:
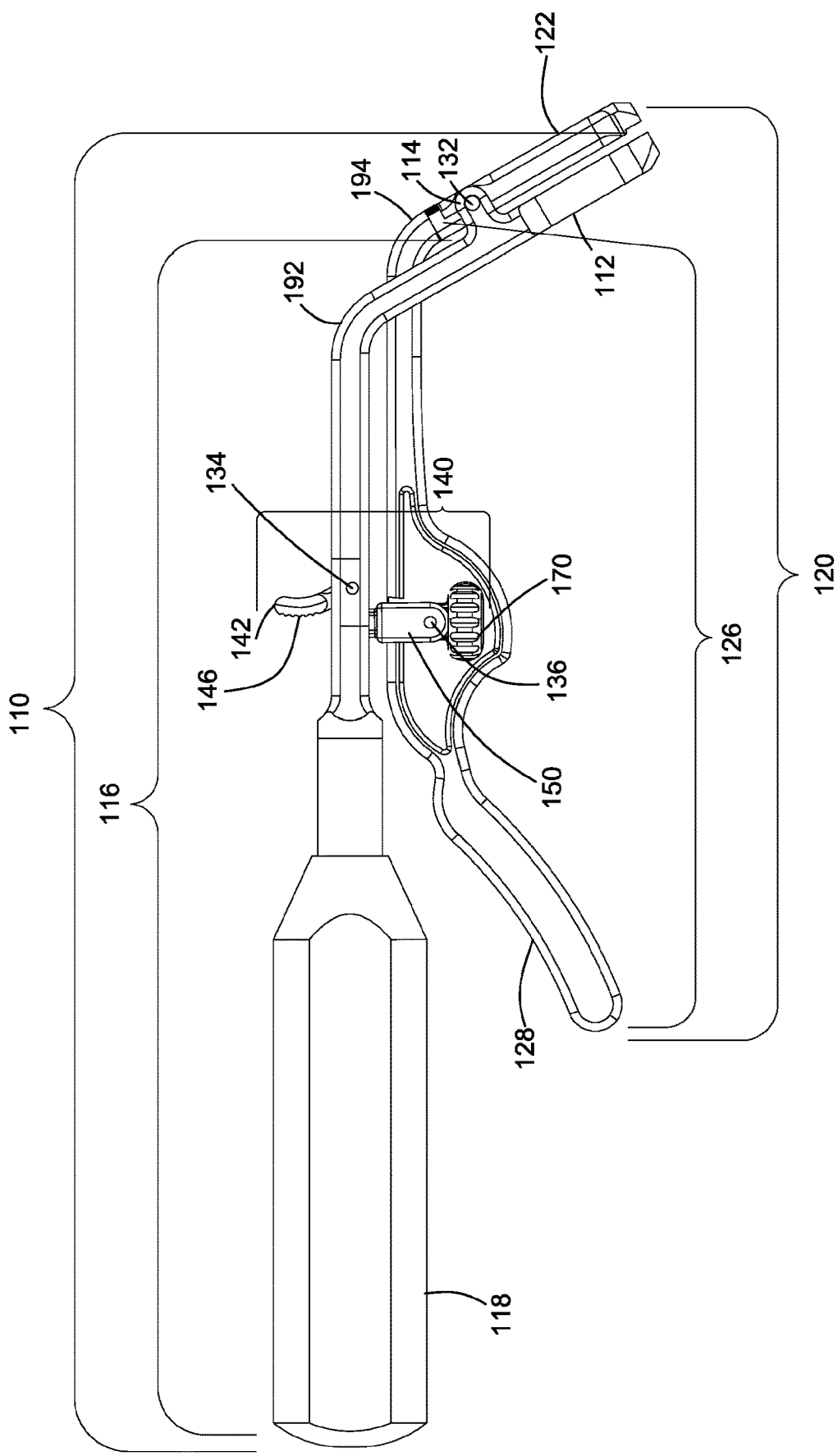
FIG. 4 is a second side view of the tool.
Figure 7:
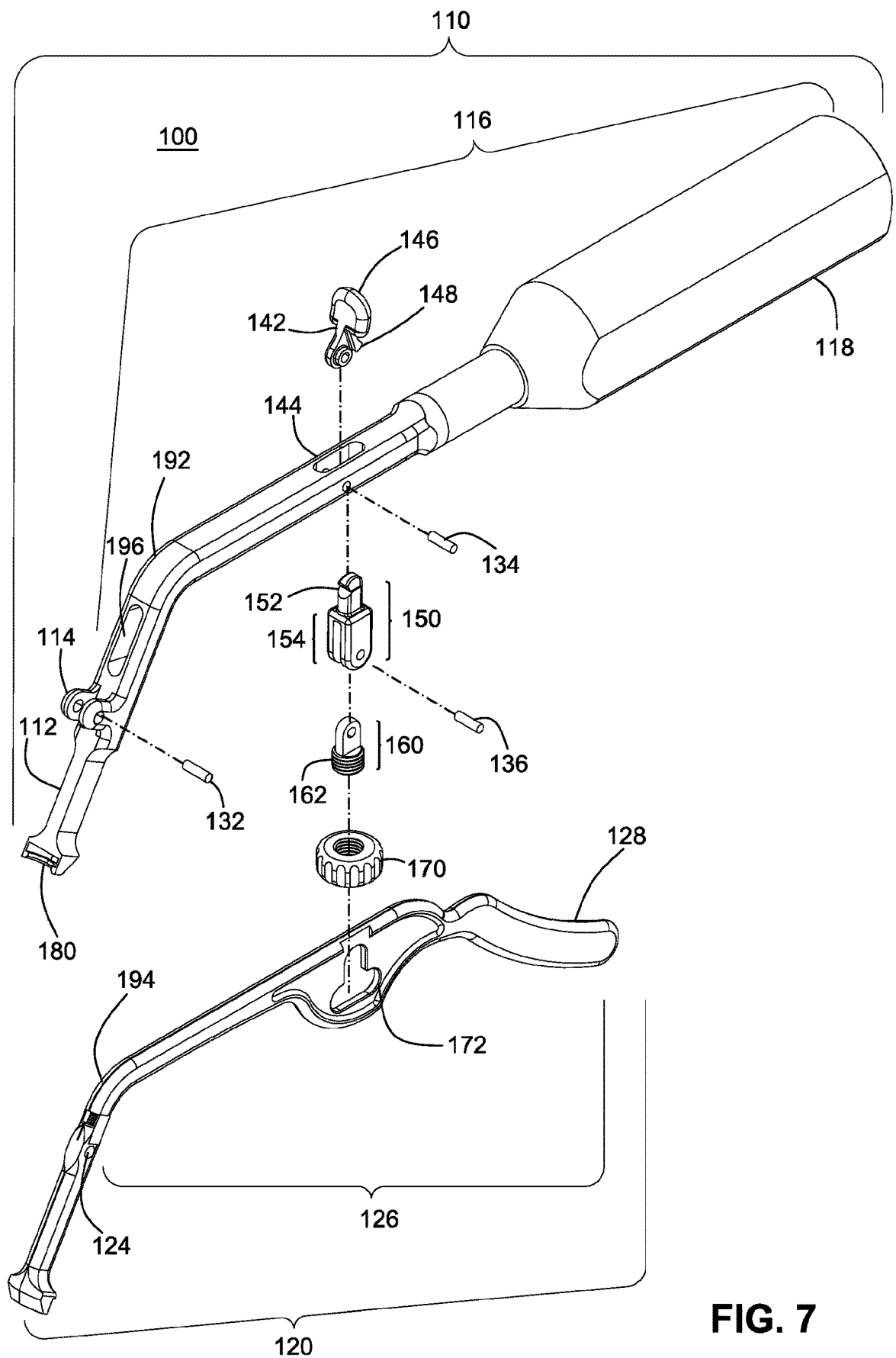
FIG. 7 is an exploded view of the tool.
Figure 8:
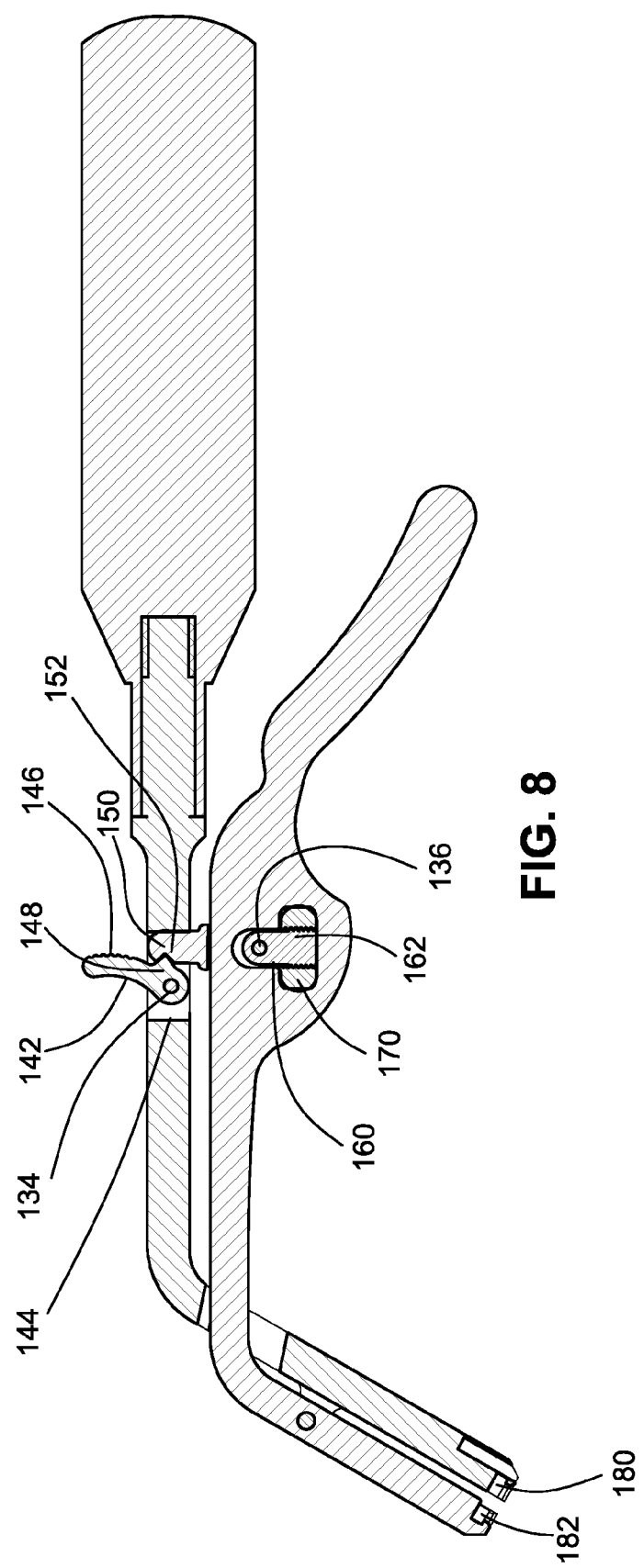
FIG. 8 is a cross section of the tool.
Figure 9:
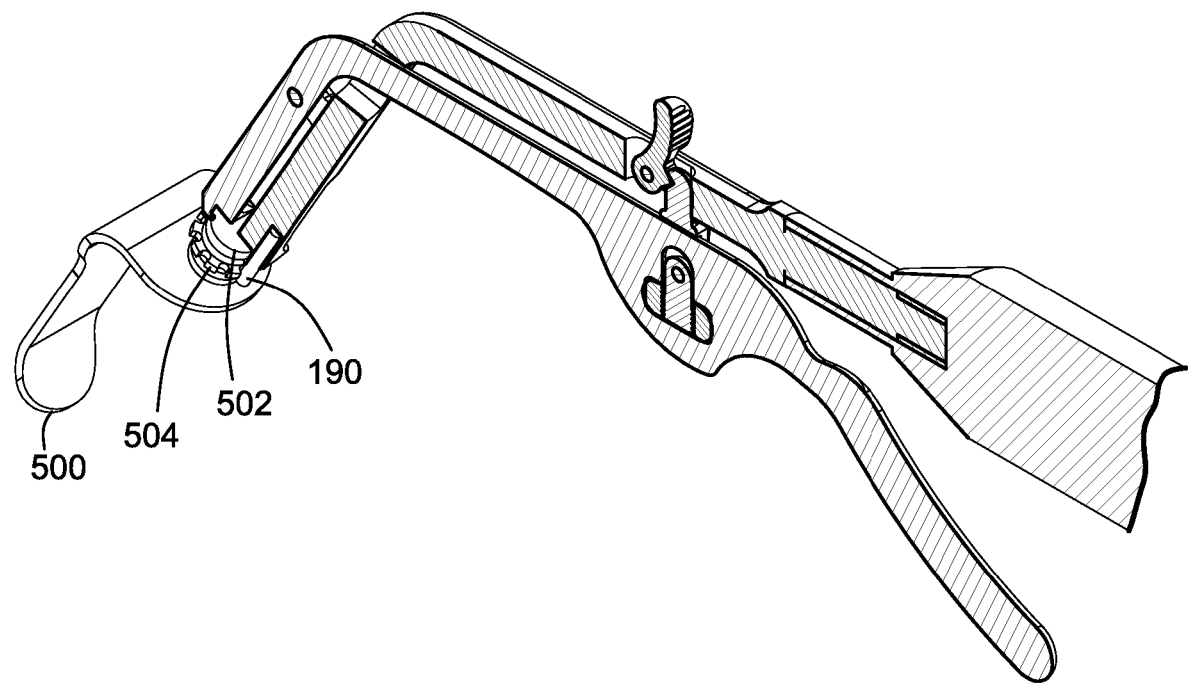
FIG. 9 is a cross section taken of the tool in a closed position, engaged with and holding a retractor blade (not in cross section) grasped by the tool.

FIG. 1 illustrates a tool 100, in the form of a handle for holding a retractor blade 500 (illustrated elsewhere, e.g., in FIG. 9). It should be appreciated that handle 100 may form part of a retractor system, including one or more retractor blades 500, and a retractor frame (not shown). The retractor frame may include one or more connector heads, such as are described in U.S. Pat. No. 6,887,197, which is incorporated by reference in its entirety. The tool 100 includes a first arm 110 and a second arm 120. The first arm 110 includes a first jaw portion 112, a first rotatable connection 114 and a first handle portion 116. The first handle portion 116 includes a first grip portion 118. The second arm includes a second jaw portion 122, a second rotatable connection 124 and a second handle portion 126. The second handle portion 126 includes a second grip portion 128. The first rotatable connection 114 and the second rotatable connection 124 are illustrated as through holes connected by a pin 132 (best seen in FIG. 7), which in combination allow the first arm 110 and the second arm 120 to rotate relative to one another. In the position illustrated in FIG. 1, the tool 100 is closed. In the closed position, the first jaw portion 112 and the second jaw portion 122 are parallel and slightly spaced from one another. However, the space could be omitted, in at least one location, if it is desirable to limit clamping force applied to an object held by the tool 100. Or the jaw portions could have different shapes such that any gap between the jaw portions changes along their length in the closed position, and in such a configuration the jaw portions would not be considered parallel.

FIGS. 2-6 illustrate the same elements of the tool 100 as illustrated in FIG. 1, but with various different views.

In the illustrated embodiment, a lock mechanism 140 spans between the first handle portion 116 and the second handle portion 126 and adjacent the first and second grip portions 118, 128. The lock mechanism 140 can fix a rotational orientation of the first arm 110 relative to the second arm 120. The lock mechanism 140 may be located elsewhere, but being close to the grip portions may allow for easier use because, for example, the user may not have to move their hands as much, or at all, to transition from gripping the tool to locking the tool or vice-versa.

The components of the lock mechanism 140 described in this embodiment are most clearly illustrated in FIGS. 7-14. It should be appreciated that alternative locking mechanisms may be employed in some embodiments. The lock mechanism 140 includes a first bar 142 that is rotationally connected to the first arm 110 by way of a pin 134, where the first bar 142 and pin 134 are within an aperture 144 of the first arm 110. The first bar 142 includes an actuation portion 146 that is relatively wider than other portions of the first bar 142, thus providing a relatively larger surface area for a user to actuate the first bar 142. A protrusion 148, which is substantially triangular, interacts with a corresponding recess 152 discussed further below.

The lock mechanism 140 includes a second bar 150 rotationally connected to the second arm 120 by way of a pin 136. A first end of the second bar 150 includes a recess 152 shaped to receive the protrusion 148. The recess 152 is substantially V-shaped. A second end of the second bar 150 is a yoke 154 (e.g., U-shaped) with a hole that accepts the pin 136. The yoke 154 and pin 136 together surround a portion of the second arm 120 and thus retain the second bar 150 to the second arm 120.

The pin 136 is also connected to a third bar 160 by way of a hole in one end of the third bar 160. Opposite the hole are threads 162 (e.g., male threads) connected to a knob 170 that is also threaded (e.g., with female threads). The choice of male and female threads may be reversed, but the illustrated configuration may allow for easier manufacture than components where male and female threads are reversed with respect to the illustrated configuration.

The second arm 120 includes an aperture 172 in which the third bar 160 and knob 170 are located. The combination of the aperture 172 and the connection between the knob 170, threads 162 and yoke 154 ensure that the knob 170 and third bar 160 are retained to the second arm 120.

Rotation of the knob 170 causes relative extension or retraction of the third bar 160, which in turn causes corresponding movement of the second bar 150. When the recess 152 and the protrusion 148 are engaged, and thus when the lock mechanism 140 is locked, rotation of the knob 170 can adjust the relative rotational position of the first arm 110 to the second arm 120. This in turn allows for adjustment of the relative position of the first jaw portion 112 to the second jaw portion 122. In this way, the closed, or locked, position of the tool 100 can be adjusted between a plurality of closed positions.

If adjustment of the locked position is not desired, the third bar 160, the knob 170 and the aperture 172 can be omitted, in which case the yoke 154 would be connected to a hole in the second arm 120 by way of the pin 136.

The first jaw portion 112 includes a first recess 180 and the second jaw portion 122 includes a second recess 182. The first recess 180 and the second recess 182 are similar in that both are shaped to receive opposite sides of a component of a retractor blade 500, e.g. the recesses are negatives of the component of the retractor blade 500. As illustrated, the component of the retractor blade 500 is a disc-shaped member 502 and the first recess 180 and the second recess 182 are oriented such that a central axis of the disc-shaped member 502 is parallel to the first jaw portion 112 and the second jaw portion 122 in the closed configuration. A radius of the first recess 180 and second recess 182 are therefore normal to the central axis of the disc-shaped member 502, which is also substantially tangential to a path of movement of the first jaw portion 112 and the second jaw portion 122.

If the first recess 180 and the second recess 182 are both partial disc shapes, the first jaw portion 112 and the second jaw portion 122 can cooperate to hold the retractor blade 500 in advantageous ways. If the first recess 180 and the second recess 182 lightly contact, or are slightly spaced away from, an outer diameter of the disc-shaped member 502, the tool 100 will retain the retractor blade 500 while allowing the retractor blade 500 to rotate around a central axis of the disc-shaped member 502. If the surfaces of the first recess 180 and the second recess 182 apply a sufficiently high force to the disc-shaped member 502, relative rotation of the retractor blade will not occur or will be relatively difficult. The amount of force applied can be adjusted by rotation of the knob 170, and thus a plurality of locked positions of the lock mechanism 140 includes at least a position where the retractor blade 500 is rotatable within the tool 100 and a position where the retractor blade 500 is not rotatable.

Another way in which rotation of the retractor blade 500 relative to the jaw portions can be prevented is by inclusion of a protrusion 190. The protrusion 190 is illustrated as part of the first jaw portion 112, but the protrusion could be additionally or alternatively a part of the second jaw portion 122. As illustrated, the protrusion 190 is a pin inserted into a hole of the first jaw portion 112, but the protrusion 190 could alternatively be an extension from, and unitary with, the first jaw portion 112. In the illustrated configuration, the protrusion 190 is substantially parallel to a central axis of the disc-shaped member 502.

The protrusion 190 interfaces with a space between adjacent protrusions on the retractor blade 500 adjacent the disc-shaped member. The alternating spaces and protrusions together form a gear-shaped member 504 of the retractor blade. Using such a combination of spaces between protrusions allows for the retractor blade 500 to be indexed between a plurality of rotational positions corresponding to a number of spaces. Thus if there are eight spaces, the retractor blade 500 can be held in eight different rotational positions with respect to the tool 100, i.e., in 45° increments.

Alternatively, the protrusion 190 could be within the first recess 180 and/or the second recess 182. If located within the first recess 180 or second recess 182, the disc-shaped member 502 would include a corresponding notch or recess 506. If the protrusion 190 is included in both the first recess 180 and the second recess 182, the disc-shaped member 502 may include at least two notches 506, which may be diametrically opposed from one another (i.e., 180° apart). Of course, any number of notches 506 may be provided, and higher numbers of notches will result in the disc-shaped member 502 being similar to a gear shape. If the protrusion 190 is included within the first recess 180 or the second recess 182, the protrusion 190 may be constructed in the same manner explained above, e.g., by inserting a pin into a hole, where the pin would be within the outer perimeter of the first recess 180 or second recess 182, respectively, or by forming the protrusion 190 as a unitary part of the first jaw portion 112 or second jaw portion 122.

The protrusion 190 and adjustability of the lock mechanism (e.g., inclusion of the threads 162 and knob 170) may be considered alternative ways to prevent relative rotation of the retractor blade 500. Thus if the protrusion 190 is included, then it may not be necessary to provide adjustment in the lock mechanism 140 because both the protrusion 190 and an appropriately adjusted lock mechanism 140 may prevent relative rotation of the retractor blade 500. And if adjustment of the lock mechanism 140 is included, the protrusion 190 may not be required. But both mechanisms can be provided simultaneously in the tool 100.

Each of the first arm 110 and the second arm 120 include a respective bend 192, 194, which are both in the same angle and direction. The bends 192, 194 provide at least two functions. First, the bends 192, 194 control the relative angle between the first grip portion 118 and the retractor blade 500. This may allow for optimization between the relative positions of these two components. Second, the bend allows for the second arm 120 to extend through an aperture 196 in the first arm 110. With the aperture 196 in the disclosed location, an edge or surface of the aperture 196 nearest the first rotatable connection 114 may limit a maximum opening angle of the tool 100 because the second arm 120 will contact the edge or surface at or adjacent the bend 194 and thus limit the maximum opening angle.

To use the tool 100, a user may grasp the first grip portion 118 in one hand while using at least one finger of that hand to manipulate the second grip portion 128. When the disc-shaped member 502 is within the first and/or second recesses 180, 182, the first grip portion 118 and the second grip portion 128 are drawn together until protrusion 148 and the recess 152 of the lock mechanism 140 are engaged. During this engagement process, the second bar 150 enters the aperture 144 and pushes the first bar 142 out of the way (e.g., causing the actuation portion 146 to rotate away from the first grip portion 118) until the second bar 150 has moved far enough for the protrusion 148 to move into the recess 152. Once the protrusion 148 and the recess 152 are engaged, the first bar 142 and the second bar 150 may reverse their respective movements to complete the locking operation. When in the locked condition, the second bar 150 is retained between the protrusion 148 and a wall of the aperture 144. The user may press the actuation portion 146 away from the first grip portion 118 to reverse the locking procedure (i.e., unlock the tool 100). With the tool 100 locked, the user may hold the first grip portion 118 to manipulate the retractor blade 500, which is securely held between the first jaw portion 112 and the second jaw portion 122.

Figure 10:
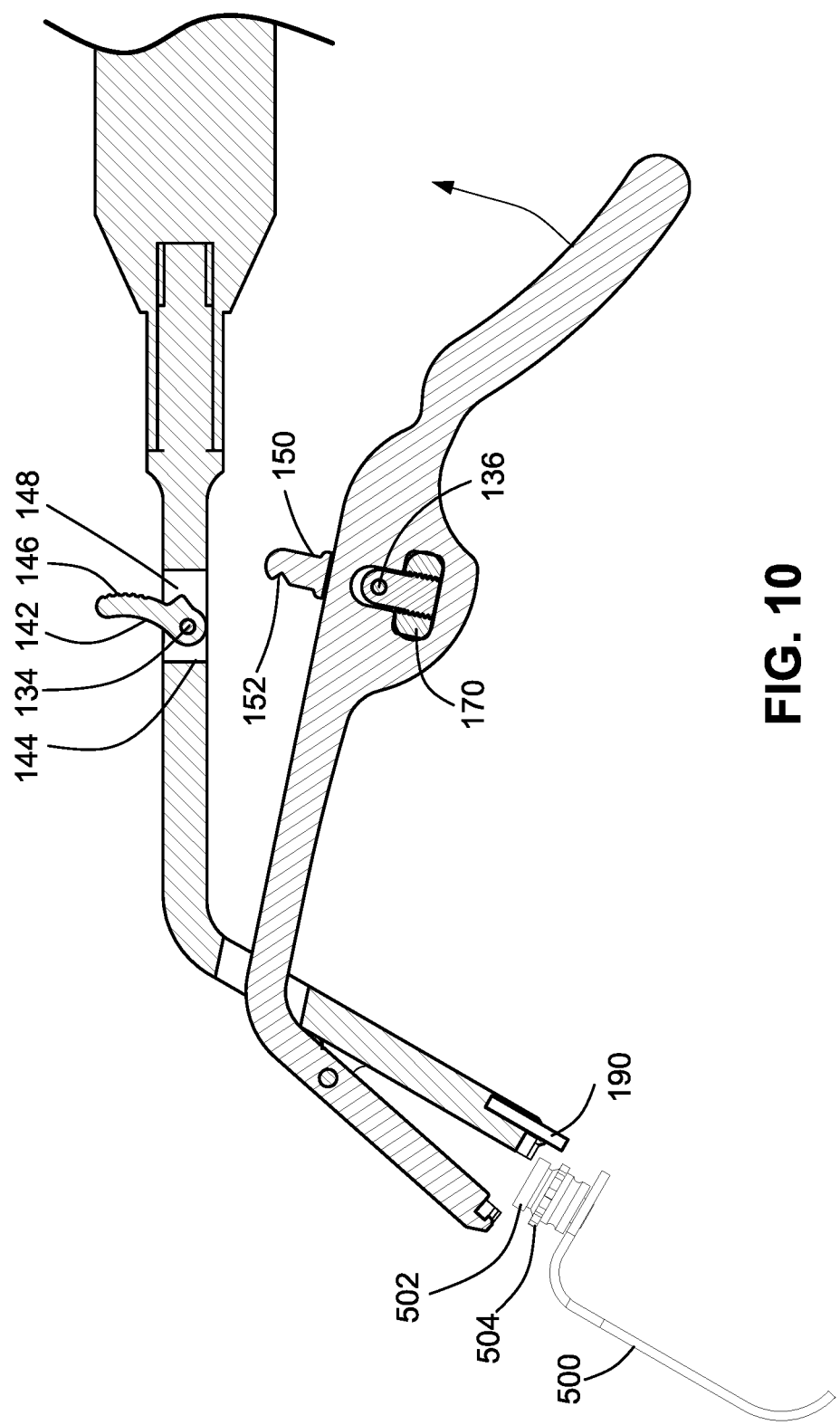
FIG. 10 is a cross section taken of part of the tool in an opened position, with a retractor blade (not in cross section).
Figure 11:
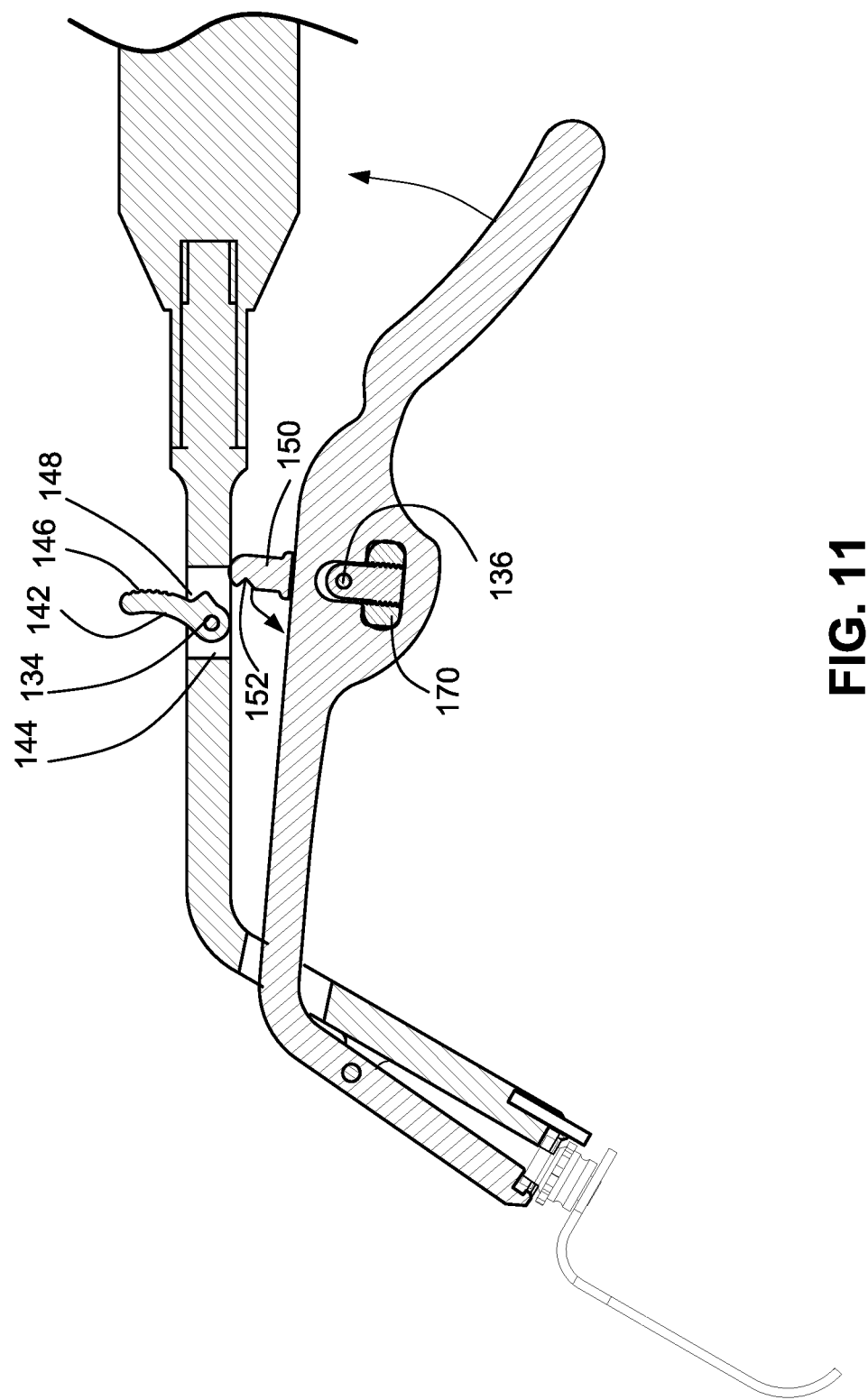
FIG. 11 is a cross section taken of part of the tool in a closed position, engaged with and holding a retractor blade (not in cross section) in an unlocked position.
Figure 12:
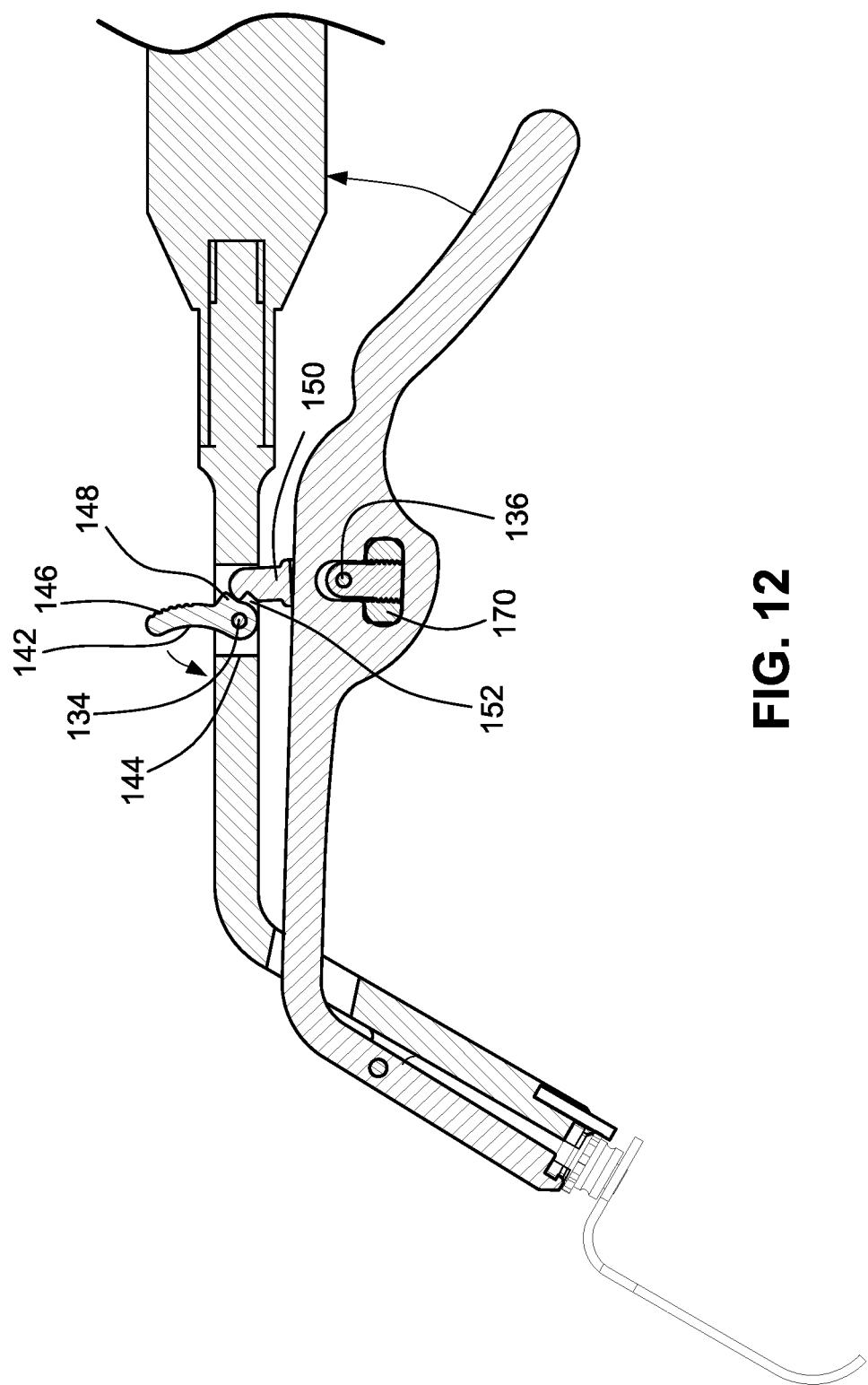
FIG. 12 is a cross section taken of part of the tool in a closed position, engaged with and holding a retractor blade (not in cross section) in an unlocked position.
Figure 13:
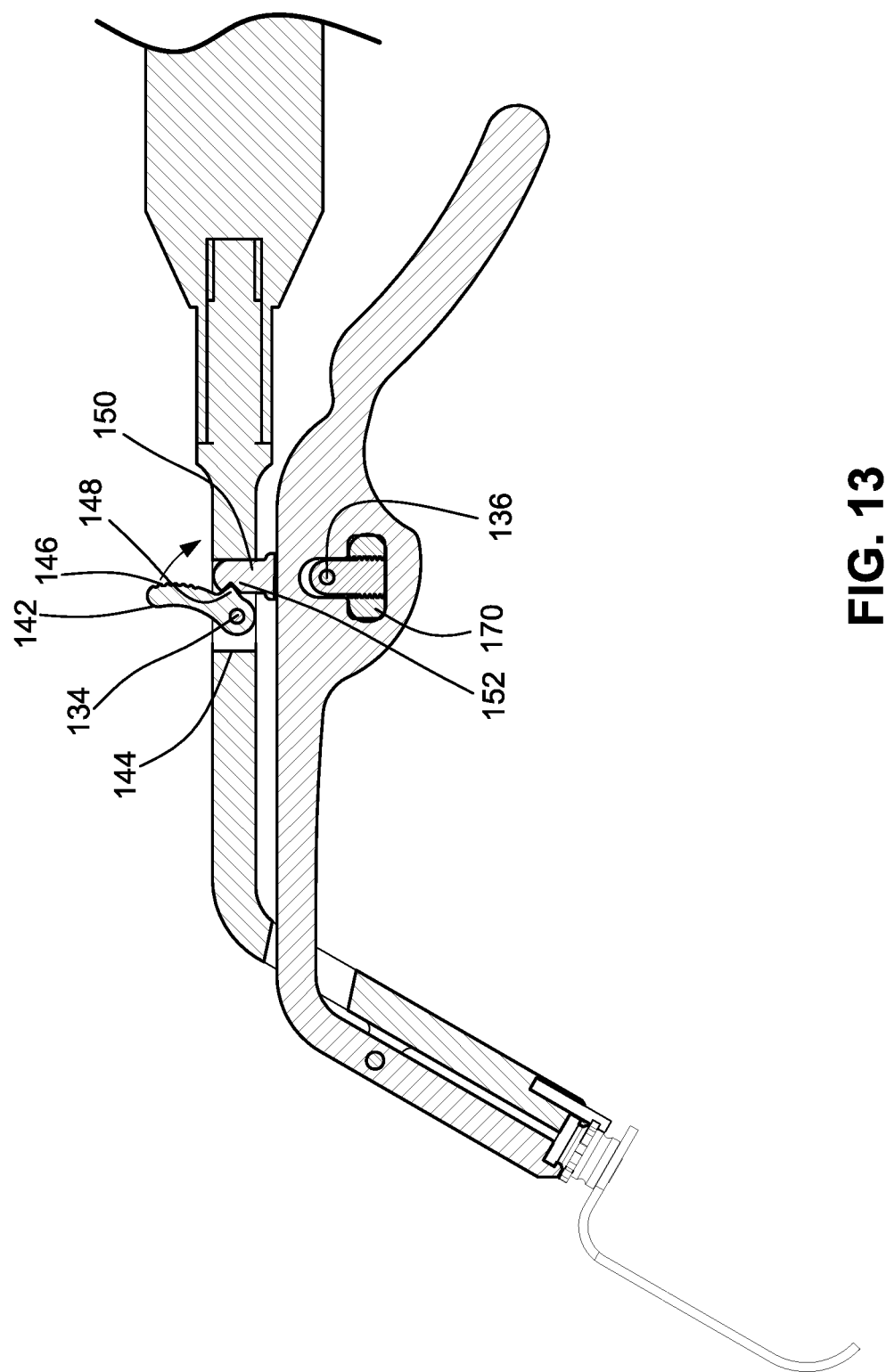
FIG. 13 is a cross section taken of part of the tool in a closed position, engaged with and holding a retractor blade (not in cross section) in a locked position.

FIGS. 10-13 illustrate movement of the components of the lock mechanism 140. FIG. 10 illustrates the position where the second bar 150 is in contact with an edge of the aperture 144. In FIG. 11, the second bar 150 has rotated counter-clockwise (relative to the position of FIG. 10) such that the second bar 150 can move into the aperture 144. In FIG. 12, the second bar 150 has moved into the aperture 144 such that the second bar 150 is in contact with the protrusion 148 and further movement of the second bar 150 into the aperture will cause rotation of the first bar 142 counter-clockwise. FIG. 13 illustrates the position where the second bar 150 extends sufficiently far into the aperture 140 that the first bar 142 has rotated clockwise and the protrusion 148 is engaged with the recess 152. Although not illustrated, there may be a spring that biases the first bar 142 to rotate in the clockwise direction in these figures. If such a spring is included, the lock mechanism 140 may automatically lock once the second bar 150 is a predetermined distance within the aperture 144. If the spring is omitted, it may be necessary for a user to rotate the first bar 142 clockwise to the position illustrated in FIG. 13.

FIGS. 14A and 14B illustrate another configuration of the retractor blade 500 in isolation. The retractor blade 500 differs in that there are two disc-shaped members 502, instead of a disc-shaped member and a gear-shaped member as described above. In this embodiment, the two disc-shaped members 502 are similar in that notches 506 are included in both, but the rotational orientation of the notches 506 is offset by 90° between the two disc-shaped members 502. It should be appreciated that the shape of the notch may vary from the shape shown in FIGS. 14A and 14B, without deviating from the present approach. With this configuration, the tool 100 can grasp one of the disc-shaped members 502 (e.g., the one furthest away from the body 508, at the upper portion of the blade's hub) and then another tool (e.g., a frame to hold the retractor 500 during use (such as is disclosed in U.S. Pat. No. 6,887,197 and incorporated herein by reference) may use the other disc-shaped member 502 to fix the orientation of the retractor blade. The handle may include one or more protrusions configured to mate with at least one upper notch 506. Likewise, the other tool, such as a retractor frame, may include one or more protrusions configured to mate with at least one lower notch 506. Embodiments featuring offset notches allow for greater control and precision when transitioning the retractor blade from the handle to the retractor frame. With the notches 506 offset in this manner, the likelihood of grasping the incorrect one of the two disc-shaped members 502 is significantly reduced. Additionally, the orientation of the blade relative to both the handle 100 and the retractor frame (not shown) is fixed, which advantageously improves the accuracy and consistency of using the retractor system during surgical procedures. It should be appreciated that a retractor system may include two handles, one with at least one protrusion corresponding to a notch, and one without the protrusion, allowing the user to determine whether the retractor blade may rotate in the handle. Similarly, a retractor frame may include one or more connector heads, some with at least one corresponding protrusion, and some without a protrusion, allowing the user flexibility in determining whether the retractor blade is free to rotate.

Although the terms first, second, primary, secondary, etc. may be used herein to describe various elements, these elements should not be limited by these terms. These terms are only used to distinguish one element from another. For example, but not limiting to, a first element could be termed a second element, and, similarly, a second element could be termed a first element, without departing from the scope of example embodiments. As used herein, the term "and/or" includes any, and all, combinations of one or more of the associated listed items. As used throughout the specification and claims, "substantially" and "about" used in conjunction with relative terminology (e.g., parallel) include at least deviations from ideal or nominal values that are within manufacturing, operational and/or inspection tolerances.

While the present technology has been described in connection with several practical examples, it is to be understood that the technology is not to be limited to the disclosed examples, but on the contrary, is intended to cover various modifications and equivalent arrangements included within the spirit and scope of the technology.

100 tool
110 first arm
112 first jaw portion
114 first rotatable connection
116 first handle portion
118 first grip portion
120 second arm
122 second jaw portion
124 second rotatable connection
126 second handle portion
128 second grip portion
132 pin
134 pin
136 pin
140 lock mechanism
142 first bar
144 aperture
146 actuation portion
148 protrusion
150 second bar
152 recess
154 yoke
160 third bar
162 threads
170 knob
172 aperture
180 first recess
182 second recess
190 protrusion
192 bend
194 bend
196 aperture
500 retractor blade
502 disc-shaped member
504 gear-shaped member
506 notch
508 body

What is claimed is:
1. A retractor blade handle comprising
a first arm that is rigid and includes a first jaw portion with a first recess, a first rotatable connection and a first handle portion, the first rotatable connection being between the first jaw portion and the first handle portion; and
a second arm that is rigid and includes a second jaw portion with a second recess, a second rotatable connection and a second handle portion, the second rotatable connection being between the second jaw portion and the second handle portion, the first rotatable connection and the second rotatable connection are connected together such that the first arm and the second arm are rotatable with respect to one another within a predetermined angular range; and
a lock mechanism configured to fix a rotational orientation of the first arm to the second arm only when the handle is in a closed position, wherein the rotational orientation is adjustable and the closed position is a subset of the predetermined angular range; wherein the first recess and the second recess are configured to simultaneously receive and retain a disc-shaped member attached to a retractor blade on opposite sides of a diameter of the disc-shaped member.

2. The handle according to claim 1, wherein the first recess and the second recess are negatives of respective portions of the disc-shaped member.

3. The handle according to claim 1, wherein the first jaw portion and the second jaw portion are together configured to prevent the retractor blade from rotating around a central axis of the disc-shaped member.

4. The handle according to claim 3, wherein the first jaw portion and the second jaw portion are together configured to clamp the disc-shaped member and apply a frictional force that prevents the disc-shaped member from rotating.

5. The handle according to claim 1, wherein one of the first jaw portion and the second jaw portion comprises a pin adapted to engage a recess of the retractor blade that is adjacent the disc-shaped member to prevent the retractor blade from rotating around a central axis of the disc-shaped member.

6. The handle according to claim 5, wherein an axis of the pin is substantially parallel to the central axis of the disc-shaped member when the disc-shaped member is retained between the first recess and the second recess.

7. The handle according to claim 1, wherein the first jaw portion and the second jaw portion are parallel in a closed configuration.

8. The handle according to claim 7, wherein the first recess and the second recess are oriented such that a central axis of the disc-shaped member is parallel to the first jaw portion and the second jaw portion in the closed configuration.

9. The handle according to claim 1, wherein the closed position allows the retractor blade to rotate around a central axis of the disc-shaped member while retaining the disc-shaped member between the first jaw portion and the second jaw portion.

10. The handle according to claim 1, wherein the closed position prevents the retractor blade from rotating around a central axis of the disc-shaped member and retains the disc-shaped member between the first jaw portion and the second jaw portion.

11. The handle according to claim 1, wherein the closed position is selectable from a plurality of closed positions.

12. The handle according to claim 11, wherein the lock mechanism comprises mated male and female threaded components that provide the plurality of closed positions by relative rotation between the male and female threaded components.

13. The handle according to claim 1, wherein the first arm includes a first bend between the first rotatable connection and the first handle portion, and the second arm includes a second bend between the second rotatable connection and the second handle portion.

14. The handle according to claim 13, wherein the first bend and the second bend are a same direction and angle.

15. The handle according to claim 1, wherein the lock mechanism comprises a first bar with a first rotational connection to the first arm and a second bar with a second rotational connection to the second arm.

16. The handle according to claim 15, wherein rotation of the first bar in a direction allows engagement of the second bar and rotation of the first bar in the direction causes release of the second bar.

17. The handle according to claim 15, wherein the second bar extends from and transverse to the second arm.

18. The handle according to claim 17, wherein the lock mechanism comprises an adjustment mechanism to adjust an amount that the second bar extends from the second arm.

19. The handle according to claim 18, wherein the adjustment mechanism comprises a rotatable knob that is threaded to a third bar such that rotation of the knob causes relative extension or retraction of the third bar, and the third bar provides the second rotational connection.

20. The handle according to claim 19, wherein the second bar comprises a yoke that includes the second rotational connection and a portion of the second arm is retained between the yoke and the third bar.

21. The handle according to claim 15, wherein the first arm comprises an aperture that contains a portion of the first bar and that is adapted to receive a portion of the second bar when the handle is in the closed position.

22. The handle according to claim 21, wherein the portion of the second bar is retained between a wall of the aperture and the portion of the first bar when the lock mechanism is in a locking position.

23. A retractor blade and handle system comprising:
a retractor blade handle having
a first arm that is rigid and includes a first jaw portion with a first recess, a first rotatable connection and a first handle portion and a first bend there between at a bending angle, the first rotatable connection being between the first jaw portion and the first handle portion, the first handle portion defining a first handle axis; and
a second arm that is rigid and includes a second jaw portion with a second recess, a second rotatable connection and a second handle portion and a second bend there between at the bending angle, the second rotatable connection being between the second jaw portion and the second handle portion, the second handle portion defining a second handle axis; wherein
the first jaw portion extends along a first axis offset from the first handle axis by the bending angle, and the second jaw portion extends along a second axis parallel with the first axis and offset from the second handle axis by the bending angle;
the first rotatable connection and the second rotatable connection are connected together such that the first arm and the second arm are rotatable with respect to one another, and
the first recess and the second recess are configured to simultaneously receive and retain a disc-shaped member on opposite sides of a diameter of the disc-shaped member; and
at least one retractor blade extending from the disc-shaped member and detachably connectable to the retractor blade handle.

24. The retractor blade and handle system according to claim 23, wherein the first recess and the second recess are negatives of respective portions of the disc-shaped member.

25. The retractor blade and handle system according to claim 23, wherein the first jaw portion and the second jaw portion are together configured to prevent the retractor blade from rotating around a central axis of the disc-shaped member.

26. The retractor blade and handle system according to claim 25, wherein the first jaw portion and the second jaw portion are together configured to clamp the disc-shaped member and apply a frictional force that prevents the disc-shaped member from rotating.

27. The retractor blade and handle system according to claim 23, wherein one of the first jaw portion and the second jaw portion comprises a pin adapted to engage a recess of the retractor blade that is adjacent the disc-shaped member to prevent the retractor blade from rotating around a central axis of the disc-shaped member.

28. The retractor blade and handle system according to claim 27, wherein an axis of the pin is substantially parallel to the central axis of the disc-shaped member when the disc-shaped member is retained between the first recess and the second recess.

29. The retractor blade and handle system according to claim 23, wherein the first jaw portion and the second jaw portion are parallel in a closed configuration.

30. The retractor blade and handle system according to claim 29, wherein the first recess and the second recess are oriented such that a central axis of the disc-shaped member is parallel to the first jaw portion and the second jaw portion in the closed configuration.

31. The retractor blade and handle system according to claim 23, further comprising a lock mechanism configured to fix a rotational orientation of the first arm to the second arm when the handle is in a closed position.

32. The retractor blade and handle system according to claim 31, wherein the closed position allows the retractor blade to rotate around a central axis of the disc-shaped member while retaining the disc-shaped member between the first jaw portion and the second jaw portion.

33. The retractor blade and handle system according to claim 31, wherein the closed position prevents the retractor blade from rotating around a central axis of the disc-shaped member and retains the disc-shaped member between the first jaw portion and the second jaw portion.

34. The retractor blade and handle system according to claim 31, wherein the closed position is selectable from a plurality of closed positions.

35. The retractor blade and handle system according to claim 34, wherein the lock mechanism comprises mated male and female threaded components that provide the plurality of closed positions by relative rotation between the male and female threaded components.

36. The retractor blade and handle system according to claim 23, wherein the first arm includes a first bend between the first rotatable connection and the first handle portion, and the second arm includes a second bend between the second rotatable connection and the second handle portion.

37. The retractor blade and handle system according to claim 36, wherein the first bend and the second bend are a same direction and angle.

* * * * *